United States Patent
Matsumoto

(10) Patent No.: US 7,354,154 B2
(45) Date of Patent: Apr. 8, 2008

(54) OPHTHALMIC IMAGE TAKING APPARATUS AND OPHTHALMIC IMAGE TAKING METHOD

(75) Inventor: Kazuhiro Matsumoto, Tochigi-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 290 days.

(21) Appl. No.: 11/144,158

(22) Filed: Jun. 2, 2005

(65) Prior Publication Data

US 2005/0270485 A1    Dec. 8, 2005

(30) Foreign Application Priority Data

Jun. 4, 2004    (JP) .............................. 2004-166672

(51) Int. Cl.
*A61B 3/14*    (2006.01)

(52) U.S. Cl. ...................... 351/206; 351/205; 351/221; 396/18

(58) Field of Classification Search ................ 351/206, 351/216, 221, 205; 396/18; 600/558
See application file for complete search history.

(56) References Cited

U.S. PATENT DOCUMENTS

| | | | |
|---|---|---|---|
| 4,265,518 A * | 5/1981 | Matsumura | 351/206 |
| 5,822,446 A * | 10/1998 | Kato | 382/128 |
| 2002/0047989 A1 | 4/2002 | Shibata | |
| 2002/0067919 A1 | 6/2002 | Shibata et al. | |
| 2002/0131017 A1 | 9/2002 | Kishida et al. | |
| 2003/0231242 A1 | 12/2003 | Matsumoto | |

FOREIGN PATENT DOCUMENTS

| | | |
|---|---|---|
| JP | 4-84932 A | 3/1992 |
| JP | 6-98859 A | 4/1994 |

OTHER PUBLICATIONS

English Abstract of JP 6-98859 A; Publication date Apr. 12, 1994; (1 page).
English Abstract of JP 4-84932 A; Publication date Mar. 18, 1992; (1 page).

* cited by examiner

*Primary Examiner*—Hung Dang
*Assistant Examiner*—Joseph Martinez
(74) *Attorney, Agent, or Firm*—Morgan & Finnegan, LLP

(57) ABSTRACT

A technique preferable for ophthalmic image taking having an image taking optical system for imaging an image on an image sensing element at different imaging magnifications is disclosed which includes an image sensing element for converting the eye-to-be-examined fundus image into digital image data; an image taking optical system for imaging the eye-to-be-examined fundus image on the image sensing element at different image magnifications; fundus illumination means for illuminating fundus at a light intensity interlocking with the imaging magnifications; and region selection means for selecting a specific region including a fundus image from the image data in accordance with the imaging magnifications. Moreover, it is characterized to lower the light intensity of the fundus illumination means by interlocking with reduction of the imaging magnifications and contract the specific region by interlocking with reduction of the imaging magnifications.

6 Claims, 3 Drawing Sheets

OPHTHALMIC IMAGE TAKING APPARATUS AND OPHTHALMIC IMAGE TAKING METHOD

BACKGROUND OF THE INVENTION

1. Field of the Invention

The present invention relates to an ophthalmic image taking apparatus having an image taking optical system for imaging an image on an image sensing element at different imaging magnifications and an ophthalmic image taking method.

2. Related Background Art

A nondissipative pupil fundus camera for recording data in various image taking media has been known so far. The nondissipative pupil fundus camera observes and aligns a person to be examined under a natural dissipative pupil state by infrared light to record the static image of a color fundus image by visible flash generated by a stroboscope light source. Therefore, when image taking light dazzles, the pupil of the person to be examined contracts. Therefore, when continuing image taking, it is necessary to wait for approx. 10 min until the pupil becomes the natural dissipative pupil.

In the case of fundus image taking of mass survey, it is requested to image-take right and left eyes of many persons. Therefore, it is temporally spatially low efficient to make a person to be examined wait until the other eye is image-taken after completing image-taking of either eye. Therefore, image taking at a low light intensity is requested so that right and left eyes can be continuously image-taken.

In recent years, the number of methods for respectively recording a fundus image by using an electronic recording camera has been increased. However, when performing image-taking at a less illumination light intensity by using the camera, the image-taking sensitivity of the camera is raised.

Moreover, images of mass survey are frequently image-taken by an image-taking person. However, to shorten the image-taking time, a method for transferring an image to a distant place by using a network line is used. However, when an image size is large, transfer requires a lot of time and the image-taking efficiency is lowered. Therefore, as disclosed in Japanese Patent Application Laid-Open No. H06-098859, a method for decreasing the capacity of image information by using an image compression technique is used. Moreover, Japanese Patent Application Laid-Open No. H04-084932 discloses a technique for cutting out and transferring only a fundus image portion.

However, in the case of the above conventional method, not only a fundus image set by raising the image-taking sensitivity but also noises such as dark current are amplified. Moreover, to decrease an image size by using a compression technique, it is necessary to use irreversible compression. Therefore, a peculiar pattern appears on an image or color information is lost.

In the case of a medical image, a raw image (raw data) which is not worked is requested and an compressed image may not be recognized as a diagnostic image. When taking out only a fundus image, the shape of the image becomes a specific shape such as a circle or ellipsoid and it cannot be correctly reproduced by general viewer software. Moreover, because the image is imaged in a small shape, it is necessary to enlarge and display the image when displaying it on a monitor in order to remove an increased margin.

SUMMARY OF THE INVENTION

It is an object of the present invention to provide a preferable technique for ophthalmic image taking having an image taking optical system for imaging an image on an image sensing element at different imaging magnifications.

To achieve the above object, one aspect of the present invention is an ophthalmic image taking apparatus comprising:

an image sensing element (17a) for converting an eye-to-be-examined fundus image (Er) into digital image data;

an image taking optical system for imaging the eye-to-be-examined fundus image (Er) on the image sensing element (17a) at different imaging magnifications;

fundus illumination means (5) for performing illumination at a light intensity interlocking with the imaging magnifications; and region selection means (33) for selecting a specific region (17c) including a fundus image from the image data in accordance with the imaging magnifications, characterized in that the light intensity of the fundus illumination means (5) is decreased by interlocking with decrease of the imaging magnifications and the specific region (17c) is contracted by interlocking with decrease of the imaging magnifications.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

The present invention is described in detail in accordance with illustrated embodiments.

Embodiment 1

Figure 1:
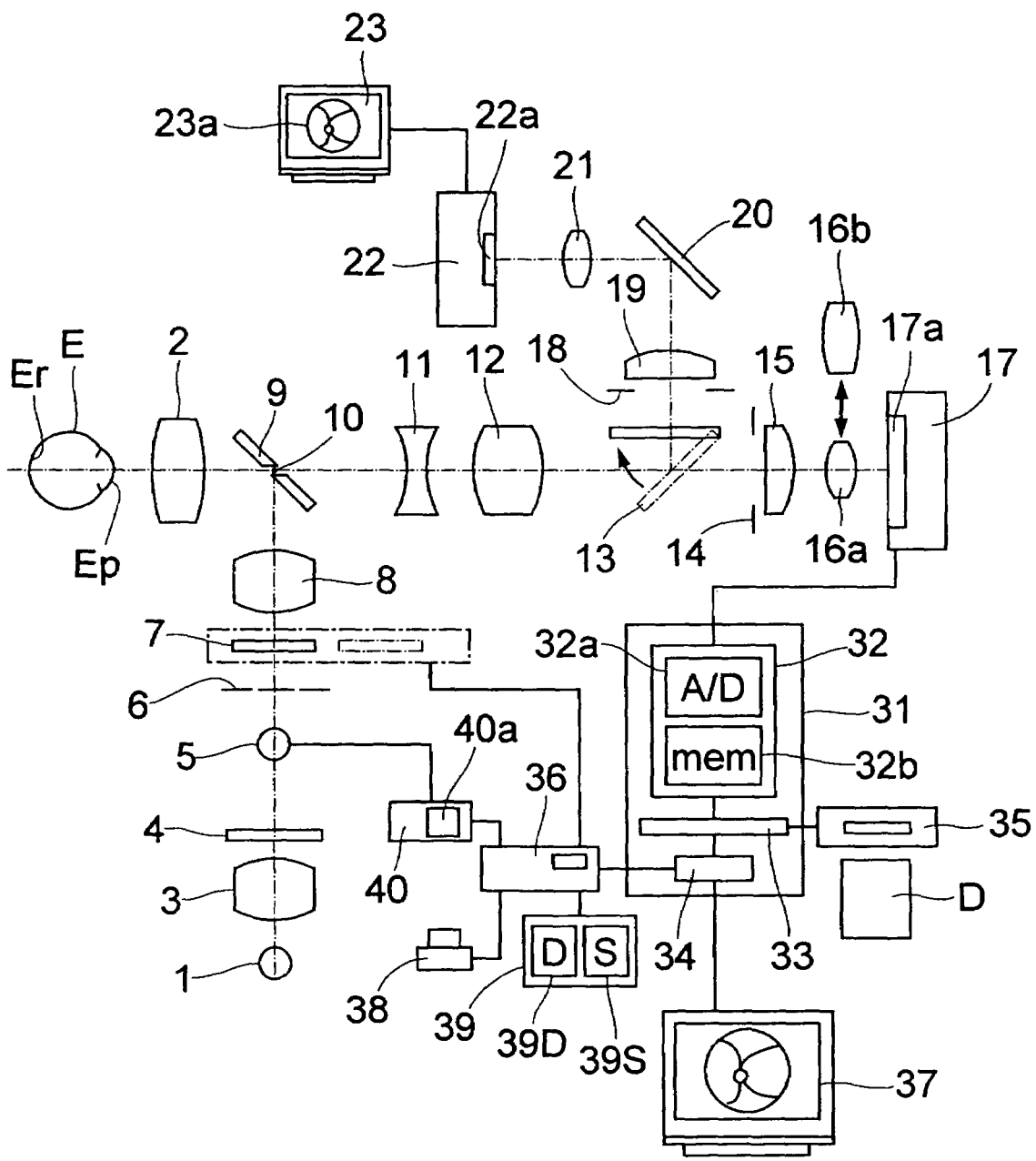
FIG. 1 is a block diagram of a fundus camera of embodiment 1.

FIG. 1 is a block diagram of a fundus camera. A condenser lens 3, a visible-light cut filter 4 for cutting off visible light but passing infrared light, a stroboscope light source 5 for emitting flash, a diaphragm 6 having an annular opening, an infrared cut filter 7 set so as to be freely inserted or removed to cut off infrared light, a relay lens 8 and a perforated mirror 9 are arranged in a range between an observation light source 1 such as a halogen lamp for emitting visible light and fixed light of infrared light and an objective lens 2.

An image-taking diaphragm 10, a focus lens 11 movable on an optical axis, an image taking lens 12, a flip-up mirror 13, a diaphragm 14, a field lens 15, relay lenses 16a and 16b to be alternately inserted into a light path and a digital camera 17 having an image sensing element 17a are arranged and fundus image taking means is constituted at the rear of the objective lens 2.

A visual field diaphragm 18, a field lens 19, a mirror 20, an image sensing lens 21 and image sensing means 22 having an image sensing element 22a are arranged in the reflective direction of the flip-up mirror 13, an output of the image taking means 22 is connected to a monitor 23 and fundus observation means is constituted.

The output of digital image data by the digital camera 17 is connected to an image control circuit 31. The image control circuit 31 is constituted of an A/D converter 32a, an image board 32 having an image memory 32b serving as memory means for storing digital image data, image control means 33 and a video RAM 34. Image recording means 35 is connected to the image control means 33 and control means 36 and a monitor 37 are connected to the video RAM 34. The recording means 35 uses a drive for writing or reading data in or from a recording medium D capable of holding a memory even if power is not supplied from the outside such as Mo, MD, DVD, card memory or hard disk.

An image-taking-mode selection switch 39 having an image taking switch 38 and switches 39S and 39D and a stroboscope control circuit 40 are connected to the control means 36. Light emission of the stroboscope light source 5 is controlled by the stroboscope control circuit 40 and the light intensity to be emitted is controlled by a voltage applied to the condenser 40a of the stroboscope control circuit 40.

In the case of image taking, an image taking person makes a person to be examined seat at the front of a fundus camera and registers an eye to be examined E and the fundus camera while observing the fundus Er of the eye to be examined E with infrared light. Under this observation state, the infrared cut filter 7 shunts to the outside of an optical path, the light emitted from the observation light source 1 is condensed by the condenser lens 3, only infrared light is transmitted by the visible-light cut filter 4 and passes through the stroboscope light source 5, the annular opening of the diaphragm 6, the lens 8 and the perforated mirror and is reflected to the left by a mirror portion around the perforated mirror 9 to illuminate the fundus Er through the objective lens 2 and the pupil Ep of the eye to be examined E.

Thus, the image of the fundus Er illuminated by infrared light passes through the objective lens 2, image taking diaphragm 10, focus lens 11 and image taking lens 12 again and is reflected upward by the flip-up mirror 13, once imaged nearby the visual field diaphragm 18, furthermore condensed by the field lens 19, reflected to the left by the mirror 20 and imaged on the image sensing element 22a of the image sensing means 22 through the image pickup lens 21. The fundus image obtained by the image sensing means 22 is converted into a video signal and displayed on the monitor 23. An image taking person performs register with the eye to be examined E by using not-illustrated operation means while viewing a fundus image 23a displayed on the monitor 23, performs focus adjustment by moving the focus lens 11 and confirms an image taking range.

The image taking person observes the fundus image 23a displayed on the monitor 23 and confirms that the image taking range, position and focus adjustment are almost preferable and then operates the switch 39S of the image-taking-mode selection switch 39 in order to perform screening image taking. The control means 36 detecting an input to the switch 39S inserts the relay lens 16a for performing contractive imaging for the relay lens 16b into the optical path, applies a voltage lower than a case of performing image taking by using the relay lens 16b to the condenser 40a of the stroboscope control circuit 40 and charges a little electric charges.

For example, when using the relay lens 16a, a fundus image having the same brightness is obtained at a light intensity to be emitted of $1/m^2$ when imaging is performed at a magnification of $1/m$ times compared to a case of using the relay lens 16b. Moreover, the image taking switch 38 is operated to image-take fundus.

The control means 36 detecting an input to the image taking switch 38 first inserts the infrared cut filter 7 for cutting off infrared light into the optical path, starts light accumulation of the digital camera 17 and transmits a light emission signal to the stroboscope control circuit 40. The stroboscope circuit 40 receiving the light emission signal transmits a trigger signal to the stroboscope light source 5 and discharges electric charges accumulated in the condenser 40a to emit light.

The light flux emitted from the stroboscope light source 5 passes through the annular opening of the diaphragm 6, infrared light is removed by the infrared cut filter 7, remaining visible light passes through the relay lens 8 and is reflected to the left by a mirror portion around the perforated mirror 9 to illuminate the fundus Er through the objective lens 2 and pupil Ep.

The fundus image thus illuminated passes through the objective lens 2, image taking diaphragm 10, focus lens 11 and image taking lens 12 again, passes through the downside of the flipped-up mirror 13 and is once imaged nearby the visual field diaphragm 14, condensed by the field lens 15 and imaged on the image taking element 17a of the digital camera 17 through the relay lens 16a. The digital camera 17 converts the image information on the whole region of the image sensing element 17a into digital image data and outputs the data to the image control circuit 31.

The image control means 33 of the image control circuit 31 cuts out an image in a previously computed range in accordance with a method to be described later and stores the image in the memory 32b. The image data is stored in the recording medium D by the recording means 35 and at the same time, reproduced to the monitor 37.

Figure 2:
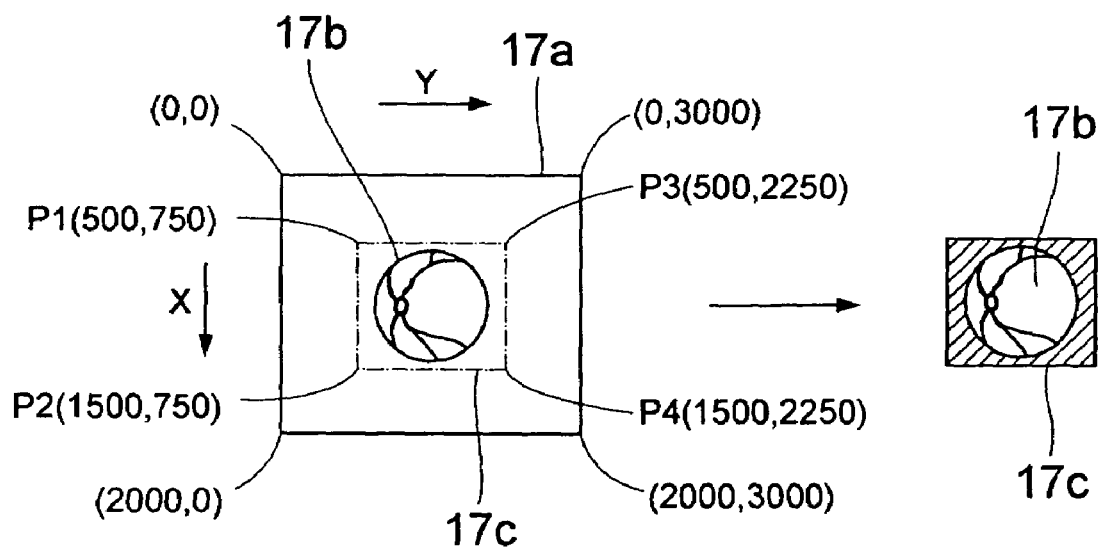
FIG. 2 is an illustration of a cutout region.

FIG. 2 shows a method for computing the cutout region of an image. For example, the image sensing element 17a of the digital camera 17 is a square pixel of 6,000,000 pixels of length 2,000×width 3,000 and the size of the effective portion is set to length 20 mm×width 30 mm.

When assuming the diameter of the image size of a fundus image in an observing mode as 9.6 mm, the fundus image 17b is image-picked up at a size smaller than the effective image pickup region (20×30) of the image sensing element 17a as shown in FIG. 2. However, the image taking range of the eye to be examined E is equal to the range observed by an image taking person through the monitor 23. Moreover, the image control means 33 cuts out a rectangular region 17c including the image pickup range. Though the calculation method of the cutout region 17c is performed as described below, it is not necessary that the region 17c is rectangular.

When assuming the top-left address of the image sensing element 17a as (0,0), longitudinal direction as X, transverse direction as Y and the address of image data as (X,Y), the size of the analogous rectangular region of length 2 to width 3 including a fundus image having a diameter of 9.6 mm, is length 10 mm×width 15 mm=1,000×1,500 pixels (1 pixel=20/2,000=0.01 mm) when considering a blank space of 2 mm at top and bottom and the center address (optical axis) becomes (1,000, 1,500).

Therefore, because it is only necessary to cut out the rectangular region centering around the center address, it is only necessary to cut out a region surrounded by four points of addresses P1 (500, 750), P2 (1,500, 750), P3 (500, 2,250) and P4 (1,500, 2,250).

The image control means 33 records the cut-out region in the recording means 35 and moreover, transfers the image to the outside through communication means according to necessity. Because the image is cut out like a rectangle, it is also possible to view an image-taken image by using an external PC (personal computer) and thereby general-purpose pure software.

Thus, by imaging an image on the image sensing element 17a at a small size, it is possible to raise the illumination intensity on an image pickup face. Therefore, it is possible to perform image taking at a small illumination light intensity. For example, when assuming the diameter of an image size as 19.2 mm when using the relay lens 16b, a fundus image having an equal brightness at an illumination light intensity of ¼ can be obtained. Thereby, it is possible to realize continuous image taking of a plurality of sheets and continuous image taking of both eyes. Therefore, it is possible to improve the image taking efficiency. Moreover, because only images in a small region are taken out and stored, a memory can be saved and recording time and transfer time can be shortened even for a raw image to which working such as compression is not applied.

When it is determined that a detailed diagnosis is necessary by observing the image thus image-taken, the switch 39D for selecting the detailed diagnostic mode of the image-taking-mode selection switch 39 is operated. The control means 36 detecting an input to the switch 39D of the image-taking-mode selection switch 39 moves the relay lens 16a to the outside of the optical path, inserts the relay lens 16b, controls the stroboscope control circuit 40 and sets the charge voltage of the condenser 40a to a high value so as to be able to illuminate the eye to be examined E with a light intensity higher than the case of the observing mode. Then, the fundus Er is image-taken by operating the image taking switch 38.

The control means 36 detecting an input to the image taking switch 38 first inserts the infrared cut filter 7 into the optical path, starts light accumulation of the image sensing element 17a of the digital camera 17 and transmits a light emission signal to the stroboscope control circuit 40. The stroboscope control circuit 40 receiving the light emission signal transmits a trigger signal to the stroboscope light source 5, discharges electric charges accumulated in the condenser 40a and emits light.

The light flux emitted from the stroboscope light source 5 passes through the annular opening of the diaphragm 6 similarly to the observation light, infrared light is removed by the infrared cut filter 7 and remaining visible light passes through the relay lens 8 and is reflected to the left by the peripheral mirror portion of the perforated mirror 9 to illuminate the fundus Er through the pupil Ep of the eye-to-be-examined E through the objective lens 2.

The fundus reflective image thus illuminated passes through the objective lens 2, image taking diaphragm 10, focus lens 11 and image taking lens 12 and passes through downside of the flipped-up mirror 13 and is once imaged nearby the visual field diaphragm 14, condensed by the field lens 15, imaged on the image sensing element 17a of the digital camera 17 by the relay lens 16b and converted into digital image data.

The image control means 33 stores the digital image data for a fundus image in the memory 32b. The image data is stored in the recording medium D by the recording means 35 and reproduced in the monitor 37. The image is displayed at a size larger than that in the screening mode.

Figure 3:
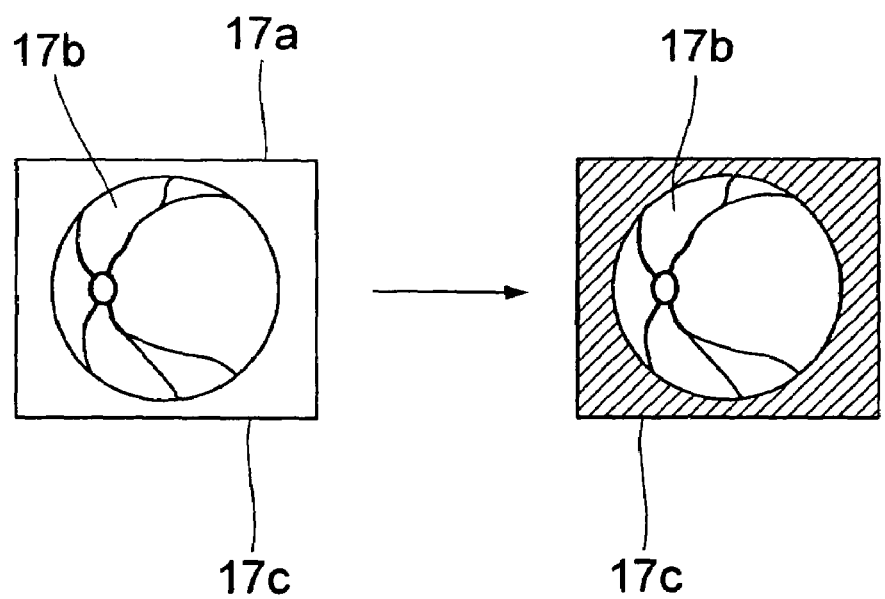
FIG. 3 is an illustration of a cutout region.

In this diagnostic mode, the fundus image 17b is largely imaged on the image sensing element 17a as shown in FIG. 3. The image taking range of the eye to be examined E is equal to the range observed by an image taking person with the monitor 23. Moreover, the image control means 33 records the whole image data in the recording means 35 without cutting out a specific region from the image data and transfers an image to the outside through communication means according to necessity.

In this case, because the capacity of the image increases, recording and communication require a lot of time and the image taking efficiency is lowered because the light intensity applied to the eye to be examined E is high. However, because a high fine image is obtained, precise diagnosis can be made and the accuracy of diagnosis is improved.

Embodiment 2

Figure 4:
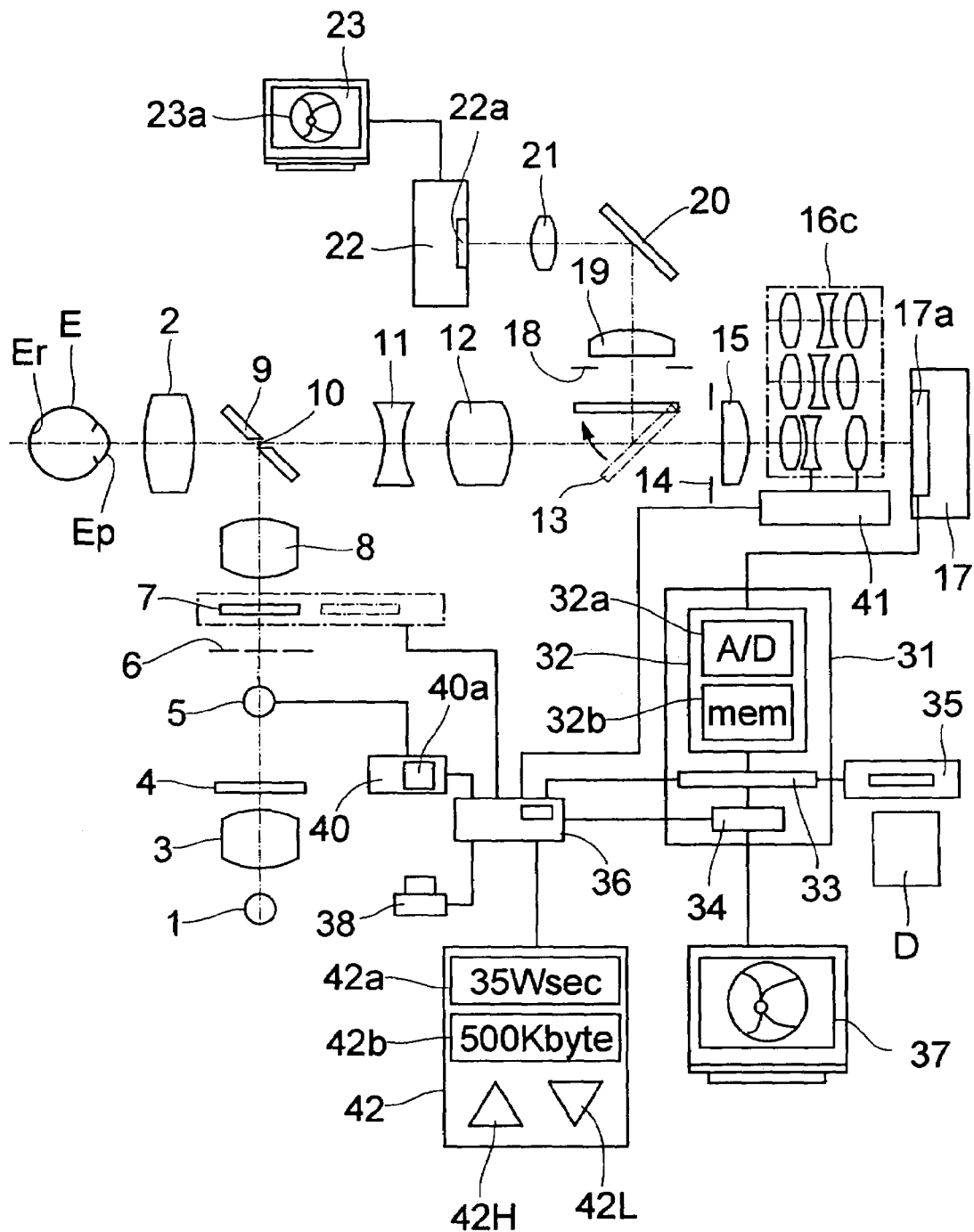
FIG. 4 is a block diagram of a fundus camera of embodiment 2.

In the case of the embodiment 1, two modes such as the diagnostic mode and screening mode are set and illumination light intensity, image taking magnification and cutout of an image are set. However, when it is possible to set a relation between desired image size and image taking light intensity in accordance with the necessity of an image taking person, the operability is further improved as shown by the embodiment 2 in FIG. 4.

In this case, release lenses 16a and 16b in FIG. 1 are replaced with a zoom lens 16c and magnifications of the zoom lens 16c can be changed by lens position control means 41 connected to the control means 36. Moreover, a mode selection switch 42 is used instead of the image-taking-mode selection switch 39 and switches 42H and 42L capable of selecting a degree of an illumination light intensity are set so that the intensity of a selected illumination light intensity and an image size are displayed on display portions 42a and 42b.

The control means 36 controls a charging voltage of the condenser 40a of the stroboscope control circuit 40 so as to output selected light-emission energy. Moreover, when controlling the lens position control means 41, each lens of the zoom lens 16c moves and the imaging magnification of an image on an image pickup face is continuously changed by following the above mentioned. The image control means 33 computes the imaging magnification, that is, a cutout region corresponding to the size of the image. Moreover, the control means 36 records the image in the cutout memory 32b in accordance with the computing result.

In this case, addresses of cutout regions P1, P2, P3 and P4 can be formed into a function as follows by assuming the diameter of the image size of a fundus image as d (mm).

When assuming the dimension of either side of a blank space to be cut out for the fundus image as 0.2 mm, the size of the cutout region becomes length d+0.4 mm and width (d+0.4)×3/2 mm. When assuming the pixel density to be 20/2000=0.01 mm, the size of the pixel to be cut out becomes length (d+0.4)/0.01 pixel and width (d+0.4)×3/2/0.01 pixel and the center address becomes (1,000, 1,500).

Therefore, the following are obtained:
P1{1,000−(d+0.4)/0.01/2, 1,500−(d+0.4)×3/2/0.01/2),
P2{1,000+(d+0.4)/0.01/2, 1,500−(d+0.4)×3/2/0.01/2},
P3{1,000−(d+0.4)/0.01/2, 1,500+(d+0.4)×3/2/0.01/2} and
P4{1,000+(d+0.4)/0.01/2, 1,500+(d+0.4)×3/2/0.01/2}.

However, when the address P1 becomes smaller than (0,0), cutting-out is not performed.

According to the present invention, it is possible to provide a technique preferable for ophthalmic image taking having an image taking optical system for imaging an image on an image sensing element at different imaging magnifications.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2004-166672 filed on Jun. 4, 2004, which is hereby incorporated by reference herein.

What is claimed is:

1. An ophthalmic image taking apparatus comprising:
   an image sensing element for taking a fundus image of an eye to be examined and making an image data;
   a switch for changing over an image taking mode between a screening mode for taking images in a mass survey and a detailed diagnostic mode for examining a taken image more detailedly than a case of observing the images taken in the screening mode;
   an image taking optical system capable of varying an imaging magnification for the fundus image imaged on the image sensing element;
   an illumination unit for illuminating a fundus of eye to be examined;
   a control unit for controlling the image taking optical system so as to make the imaging magnification of the fundus image lower than that in the case of the detailed diagnostic mode and controlling a light intensity of illumination light of the illumination unit lower than that in the case of the detailed diagnostic mode, when the switch designates the screening mode; and
   an image control unit for outputting an image data obtained by the image sensing element to a monitor when the switch designates the detailed diagnostic mode, and for outputting a specific image data which is obtained by cutting out a region including the fundus image from the image obtained by the image sensing element to the monitor when the switch designates the screening mode.

2. The ophthalmic image taking apparatus according to claim 1, further comprising a memory unit for storing the specific image data when the switch designates the screening mode.

3. The ophthalmic image taking apparatus according to claim 2, wherein the specific region is rectangular.

4. The ophthalmic image taking apparatus according to claim 1, wherein the image taking optical system has a relay lens and the imaging magnifications are changed by changing the relay lens.

5. The ophthalmic image taking apparatus according to claim 1, wherein the region for cutting out the image obtained by the image sensing element is rectangular.

6. An ophthalmic image taking method comprising steps of:
   setting a mode for examining a fundus of an eye to be examined among a screening mode for taking images in a mass survey and a detailed diagnostic mode for examining a taken image more detailedly than a case of observing the images taken in the screening mode;
   setting the imaging magnification for imaging a fundus image of the eye to be examined in a case of setting the screening mode smaller than that in a case of setting the detailed diagnostic mode;
   illuminating the fundus at a light intensity interlocking with the imaging magnifications;
   taking an image of the illuminated fundus to be examined, and obtain an image data:
   in the case of setting the screening mode, cutting out a specific region from the taken image to obtain a specific image data; and
   outputting the image data in the case of setting the detailed diagnostic mode and outputting the specific image data in the case of setting the screening mode.

* * * * *